US010395908B2

(12) United States Patent
Duchoslav et al.

(10) Patent No.: US 10,395,908 B2
(45) Date of Patent: Aug. 27, 2019

(54) METHOD FOR CONVERTING MASS SPECTRAL LIBRARIES INTO ACCURATE MASS SPECTRAL LIBRARIES

(71) Applicant: DH Technologies Development Pte. Ltd., Singapore (SG)

(72) Inventors: Eva Duchoslav, Toronto (CA); Lyle Lorrence Burton, Woodbridge (CA); Ronald F. Bonner, Newmarket (CA)

(73) Assignee: DH Technologies Development Pte. Ltd., Singapore (SG)

( * ) Notice: Subject to any disclaimer, the term of this patent is extended or adjusted under 35 U.S.C. 154(b) by 215 days.

(21) Appl. No.: 15/310,845

(22) PCT Filed: May 7, 2015

(86) PCT No.: PCT/IB2015/053351
§ 371 (c)(1),
(2) Date: Nov. 14, 2016

(87) PCT Pub. No.: WO2015/186012
PCT Pub. Date: Dec. 10, 2015

(65) Prior Publication Data
US 2017/0092476 A1    Mar. 30, 2017

Related U.S. Application Data

(60) Provisional application No. 62/006,805, filed on Jun. 2, 2014.

(51) Int. Cl.
*H01J 49/00* (2006.01)
*G16C 20/90* (2019.01)

(52) U.S. Cl.
CPC .......... *H01J 49/0036* (2013.01); *G16C 20/90* (2019.02); *H01J 49/004* (2013.01)

(58) Field of Classification Search
None
See application file for complete search history.

(56) References Cited

U.S. PATENT DOCUMENTS

| 8,395,113 B2 * | 3/2013 | Grothe, Jr. .......... | H01J 49/0036 |
| | | | 250/282 |
| 2004/0031918 A1 * | 2/2004 | Schoen ............... | H01J 49/0009 |
| | | | 250/282 |

(Continued)

OTHER PUBLICATIONS

International Search Report and Written Opinion for PCT/IB2015/053351, dated Jul. 24, 2015.

*Primary Examiner* — Andrew Smyth
(74) *Attorney, Agent, or Firm* — John R. Kasha; Kelly L. Kasha; Kasha Law LLC

(57) ABSTRACT

At least one product ion mass spectrum produced by a tandem mass spectrometer is received. A chemical structure of a compound that corresponds to the at least one product ion mass spectrum is received. One or more elemental compositions are assigned to at least one peak in the at least one product ion spectrum based on the chemical structure using the processor. At least one elemental composition of the one or more assigned elemental compositions is selected for the at least one peak using the processor. The mass of the at least one peak is converted to the mass of the selected at least one elemental composition using the processor, producing a product ion mass spectrum with higher mass accuracy.

8 Claims, 15 Drawing Sheets

(56) References Cited

U.S. PATENT DOCUMENTS

| | | | | |
|---|---|---|---|---|
| 2007/0023633 A1* | 2/2007 | Wang | .................. | H01J 49/0036 250/282 |
| 2009/0173878 A1* | 7/2009 | Coon | ................. | G01N 33/6848 250/282 |
| 2012/0049058 A1* | 3/2012 | Grothe, Jr. | .......... | H01J 49/0036 250/282 |
| 2012/0108448 A1* | 5/2012 | Kuhlmann | .......... | H01J 49/0036 506/8 |
| 2012/0261568 A1* | 10/2012 | Coon | ................. | H01J 49/0027 250/282 |
| 2012/0309040 A1* | 12/2012 | Madian | .............. | G01N 33/6842 435/23 |
| 2013/0087701 A1* | 4/2013 | Ivosev | ................... | H01J 49/26 250/282 |
| 2015/0303045 A1* | 10/2015 | Cox | ................... | H01J 49/0045 250/282 |

\* cited by examiner

METHOD FOR CONVERTING MASS SPECTRAL LIBRARIES INTO ACCURATE MASS SPECTRAL LIBRARIES

CROSS REFERENCE TO RELATED APPLICATION

This application claims the benefit of U.S. Provisional Patent Application Ser. No. 62/006,805, filed Jun. 2, 2014, the content of which is incorporated by reference herein in its entirety.

INTRODUCTION

Accurate mass spectrometry/mass spectrometry (MS/MS) spectral library matching has great potential for enhancing the efficiency of unknown screening workflows. However, large-scale accurate mass spectral repositories do not currently cover as extensive a chemical space as nominal or non-accurate mass repositories do. Building of accurate mass spectral repositories is time-consuming (e.g., instrument time, availability of chemicals, etc.) and may not always be feasible.

Some work has been done on automated re-calibration of accurate mass data to improve the quality of accurate mass spectral libraries. Also, tools to automatically generate theoretical MSn spectra from just compound structures (in the absence of any MS data) have been recently developed. These tools tend to overestimate the fragments, however.

SUMMARY

A system is disclosed for converting product ion mass spectra to product ion mass spectra with higher mass accuracy. The system includes a processor. The processor receives at least one product ion mass spectrum produced by a tandem mass spectrometer, receives a chemical structure of a compound that corresponds to the at least one product ion mass spectrum, and assigns one or more elemental compositions to at least one peak in the at least one product ion spectrum based on the chemical structure. The processor further selects at least one elemental composition of the one or more assigned elemental compositions for the at least one peak, and converts the mass of the at least one peak to the mass of the selected at least one elemental composition, producing a product ion mass spectrum with higher mass accuracy.

A method is disclosed for converting product ion mass spectra to product ion mass spectra with higher mass accuracy. At least one product ion mass spectrum produced by a tandem mass spectrometer is received using a processor. A chemical structure of a compound that corresponds to the at least one product ion mass spectrum is received using the processor. One or more elemental compositions are assigned to at least one peak in the at least one product ion spectrum based on the chemical structure using the processor. A least one elemental composition of the one or more assigned elemental compositions is selected for the at least one peak using the processor. The mass of the at least one peak is converted to the mass of the selected at least one elemental composition using the processor, producing a product ion mass spectrum with higher mass accuracy.

A computer program product is disclosed that includes a non-transitory and tangible computer-readable storage medium whose contents include a program with instructions being executed on a processor so as to perform a method for converting product ion mass spectra to product ion mass spectra with higher mass accuracy.

The method includes providing a system, wherein the system comprises one or more distinct software modules, and wherein the distinct software modules comprise an input module and an analysis module. The input module receives at least one product ion mass spectrum produced by a tandem mass spectrometer. The input module receives a chemical structure of a compound that corresponds to the at least one product ion mass spectrum. The analysis module assigns one or more elemental compositions to at least one peak in the at least one product ion spectrum based on the chemical structure. The analysis module selects at least one elemental composition of the one or more assigned elemental compositions for the at least one peak. The analysis module converts the mass of the at least one peak to the mass of the selected at least one elemental composition, producing a product ion mass spectrum with higher mass accuracy.

These and other features of the applicant's teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

Figure 1:
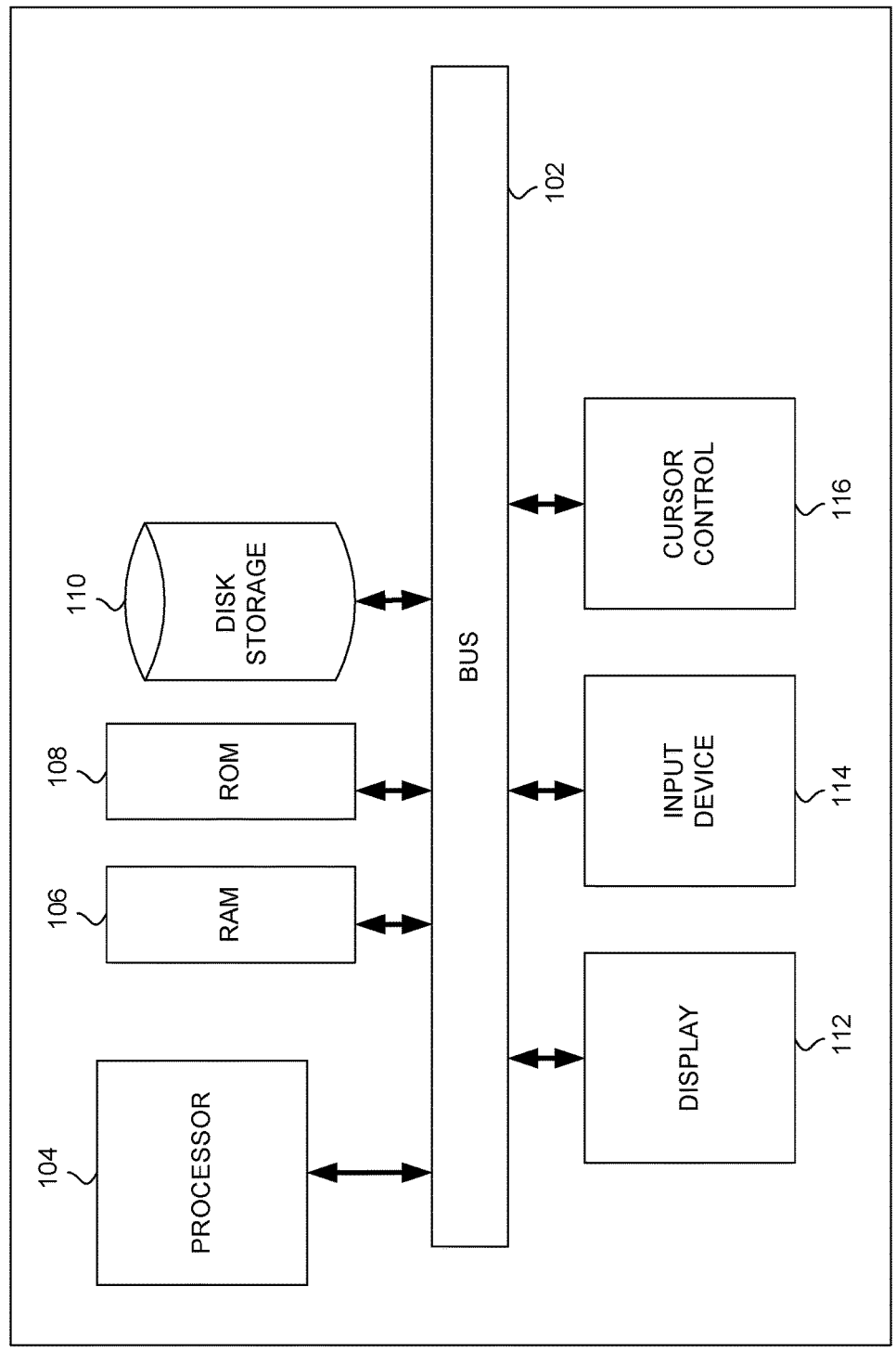
FIG. 1 is a block diagram that illustrates a computer system, upon which embodiments of the present teachings may be implemented.

Before one or more embodiments of the present teachings are described in detail, one skilled in the art will appreciate that the present teachings are not limited in their application to the details of construction, the arrangements of components, and the arrangement of steps set forth in the following detailed description or illustrated in the drawings. Also, it is to be understood that the phraseology and terminology used herein is for the purpose of description and should not be regarded as limiting.

DESCRIPTION OF VARIOUS EMBODIMENTS

Computer-Implemented System

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The one or more computer systems can include one or more web servers, for example. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Systems and Methods for Converting Masses

Tandem mass spectrometry or mass spectrometry/mass spectrometry (MS/MS) is used to identify unknown compounds by matching experimentally obtained product ion spectra with reference product ion spectra obtained from authentic standard samples of known compounds. The measured masses reflect the elemental compositions and structures of the product ions generated by fragmenting a precursor ion of the standard sample. Typically only the monoisotopic form of the precursor ion is selected so that the product ion spectrum contains no information about isotope peaks. A collection of reference product ion spectra is known as a library and the masses and intensities of the library of product ion spectra are often stored in a database.

Matching is performed by comparing the masses and intensities of peaks in the different spectra. Since there is always an error associated with mass measurements, the mass comparison uses a tolerance window to decide if two masses are the same. However, if the tolerance window is large, it is possible that ions with different but similar masses can be incorrectly assumed to match. Thus, the accuracy of the matching process depends on the measurement accuracy of the masses in both the experimental and reference spectra.

Many libraries have been generated using tandem mass spectrometers with a mass measurement accuracy on the order of 0.1 mass units (amu or Daltons, Da), such as triple quadrupole instruments, and the experimental spectra obtained on a similar instrument.

Recently it has become increasingly common to measure mass spectra using instruments that are capable of much higher accuracy, for example 0.01 or 0.001 amu. While experimental spectra from these mass spectrometers can be matched with library spectra obtained on lower accuracy devices, the performance of the spectral comparison is greatly improved if the library also contains high accuracy spectra. Normally, generating a high accuracy library requires that the standard samples be re-analyzed using a different, high accuracy instrument but this is time consuming and may not be feasible if the standards are no longer available for example.

In various embodiments, systems and method are used to improve the accuracy of an existing library, i.e., to replace nominal or low accuracy mass values with high accuracy equivalents, or the calculated exact mass, while retaining the intensity ratios of the reference spectrum.

This can be achieved if the structure of the fragment ions can be determined, since this provides the elemental composition from which the exact mass can be calculated and used to replace the low accuracy value in the reference library. It is possible to manually annotate spectra by assigning structures to the observed fragment ions, but this is time consuming and requires extensive knowledge and experience.

In various embodiments, an algorithm generates all potential elemental compositions of fragments in-silico based on a computer readable representation of the chemical structure of the known compound, but such an algorithm often predicts too many fragments. A computer readable representation of the chemical structure is, for example, a MOL file, or can be represented in SMILES notation. Furthermore, since the library spectra have low accuracy, it is common for two or more predicted fragments to have masses that match an observed fragment within the tolerance of the reference data.

In various embodiments, the algorithm further scores predicted fragments based on fragmentation rules. Fragmentation rules can include, but are not limited to, rules such as a rule that the elemental composition of fragment ions must be consistent with the composition of the (known) precursor ion, a rule that losses (which are often easier to assign) must also be consistent with their precursor, a rule that chemical bonds between carbon (C) and heteroatoms such as nitrogen (N), oxygen (O) and sulphur (S) are easier to break than C—C bonds, a rule that rings are harder to break than linear structures, especially if the ring is also aromatic. In addition, if there are families of compounds, such as drugs that are derivatives of a common scaffold structure, a structure assigned to a fragment in one member of the family is likely to be the same as a fragment with the same mass in a second member of the family.

Based on these scores, each product ion of each product ion spectrum is annotated with the most likely structure of that product ion, the elemental composition of that structure is determined, and the calculated exact mass of that elemental composition is used to update the reference library mass.

Further, if a fragment has two or more possible structures that cannot be resolved, both can be stored. In other words, if applying in silico fragmentation and fragmentation rules results in two or more possible exact masses for a product ion, the reference library can be made to store two or more mass values for a product ion.

In various embodiments, subsequent spectral matching algorithms are modified to select the mass closest to the experimental mass. For example, a reference library may receive and store masses of 99.9 and 100.1 for a peak of a product ion spectrum of a compound. These values are found through in silico fragmentation and the fragmentation rules described above. If an experimental value of 99.91 is then later found, a matching algorithm uses the exact mass closest to the experimental mass and ignores any alternative exact mass values. In this case, the exact mass closest to the experimental mass is 99.9. In various embodiments, rather than modifying the matching algorithm, the alternative exact mass values are removed from the reference library.

In various embodiments, from the elemental composition of the product ion the expected isotope pattern (masses and intensities) can be calculated and these additional peaks can be added to libraries intended for use with techniques that deliberately use wide precursor ion windows so that isotopes are included. Such techniques that deliberately use wide precursor ion windows include, but are not limited to, data independent acquisition (DIA) and sequential windowed acquisition (SWATH).

Figure 2:
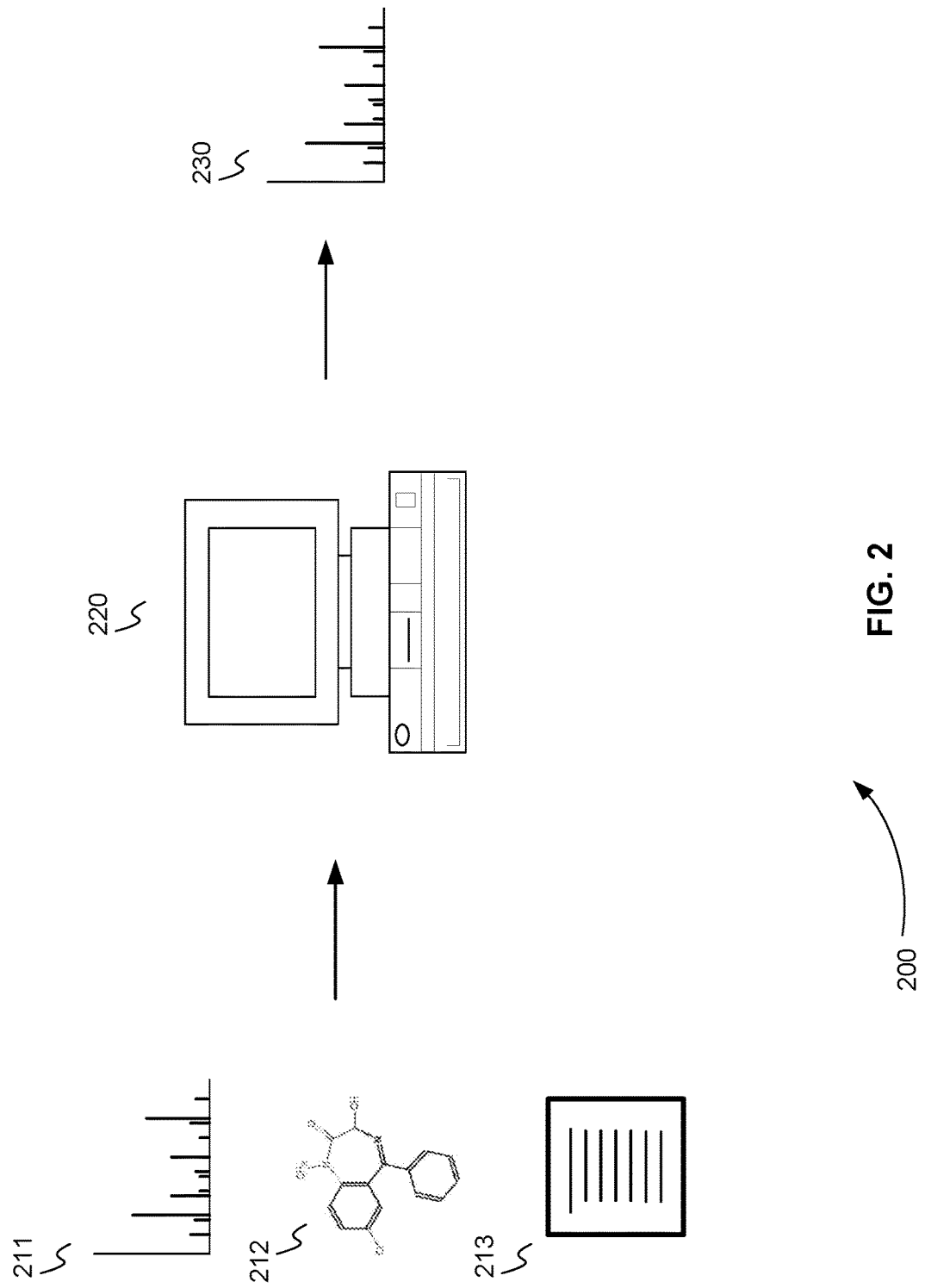
FIG. 2 is a schematic diagram of an exemplary system for converting product ion mass spectra to product ion mass spectra with higher mass accuracy, in accordance with various embodiments.

FIG. 2 is a schematic diagram of an exemplary system 200 for converting product ion mass spectra to product ion mass spectra with higher mass accuracy, in accordance with various embodiments. System 200 includes processor 220.

Processor 220 receives product ion spectrum 211 and chemical structure 212 of a compound known corresponding to product ion spectrum 211. Product ion spectrum 211 is from an existing library that has low accuracy mass values, for example.

Chemical structure 212 can also be obtained from the existing library. Typically one of ordinary skill in the art thinks of an existing library as a single database that contains the spectra and (usually) chemical structures. However, Chemical structure 212 can also be obtained from some computer directory where it is stored, or from a searchable database of chemical structures where a structure is obtained in response to a compound identifier (name, etc.).

In addition to product ion spectrum 211 and chemical structure 212, algorithm 200 can also receive complementary information 213 as input from the existing library. Complementary information 213 can include, but is not limited to, data collection conditions such as polarity, Q1 resolution, precursor m/z, m/z error distribution, target product ion spectrum Q1 width, and collision energy.

Processor 220 converts a mass peak of product ion spectrum 211 to a more accurate or exact mass peak by assigning one or more elemental compositions to the mass peak and selecting at least one elemental composition for the mass peak. Processor 220 can perform this conversion in at least two different ways.

First of all, processor 220 can perform in-silico fragmentation of chemical structure 211 and compare the masses of the elemental compositions of each simulated fragment to each mass peak of product ion spectrum 211. The elemental compositions of fragments whose masses are within a mass tolerance of the mass of the mass peak of product ion spectrum 211 are assigned to the mass peak. The assigned elemental compositions can also be given a score. The score can be based on fragmentation rules that take into account, for example, the number of broken bonds, the type of broken bonds (in light of CE used for fragmentation), the type of internal bonds, evidence of cascading fragmentation, hydrogen migration, rearrangements, and evidence of fragments in the product ion spectrum from compounds of similar structures.

At least one assigned elemental composition is then selected for the mass peak of product ion spectrum 211 based on the highest score, for example. The mass of the mass peak is then converted to the higher accuracy or exact mass of the selected elemental composition. After converting all mass peaks of product ion spectrum 211, processor 220 outputs higher accuracy product ion spectrum 230.

Processor 220 can also covert the masses of product ion spectrum 211 by first calculating all possible elemental compositions for each mass peak in product ion spectrum 211 based on the number and type of elements in chemical structure 212. As a result, processor 220 assigns one or more elemental compositions to a mass peak of product ion spectrum 211. These assigned elemental compositions can also be given a score. The score is, for example, a composition score based on mass or m/z error. In various embodiments, some mass peaks of product ion spectrum 211 can be determined to be isotopic peaks based on the Q1 width and can be given an appropriate elemental composition.

However, assigning elemental compositions for each mass peak based on mass alone may result in too many elemental compositions for some peaks, making selection of one elemental composition difficult. As a result, in various embodiments, processor 220 additionally performs in-silico fragmentation of chemical structure 211 as described above. However, in this case, instead of comparing the fragments to the mass peaks, the fragments are compared to the elemental compositions already assigned to each mass peak. As described above, the fragments can also be given a fragmentation score based on fragmentation rules. Therefore, in order to select an elemental composition, the composition score and the fragment score are combined to provide an overall score for each assigned elemental composition.

As in the other conversion method described above, at least one assigned elemental composition is then selected for the mass peak of product ion spectrum 211 based on the highest score, for example. The mass of the mass peak is then converted to the higher accuracy or exact mass of the selected elemental composition, and after converting all mass peaks of product ion spectrum 211, processor 220 outputs higher accuracy product ion spectrum 230.

Methods of converting product ion mass spectra to product ion mass spectra with a higher mass accuracy can improve accessibility and quality of internal and public spectral repositories that are used in small molecule qualitative work, such as screening and identification workflows. They can provide an easy option for bridging the compatibility limitation of the existing mass spectral libraries with accurate mass data. They can also address the discrepancy between spectral repositories collected with unit Q1 resolution and the data collected with non-specific precursor ion selection.

A well-known proteomics technique also uses a method of fragment prediction. In this proteomics technique a set of proteins are in-silico enzyme digested to form peptides and their fragments are predicted and stored in a database of theoretical spectra. Experimental product ion spectra are compared to this database in order to determine which peptides are present in a sample. Peptide fragmentation is simple and well understood so fragment mass prediction is very accurate, although there is no guarantee that a particular fragment will form and the fragment intensity cannot be predicted. In contrast, the fragments produced from the fragmentation of small molecules, are difficult to predict, and the intensity ratios are an important part of the matching algorithm, hence it is advantageous to update the masses of a library of authentic product ion spectra. Also in contrast, theoretical peptide spectra are not used to increase the mass accuracy of previously stored experimental spectra.

Recently, there has been some interest in building libraries of reference spectra of authentic peptides, which may have been synthesized or observed experimentally, and thus determining the intensity ratios of the observed fragments. If these spectra are generated with low accuracy, the techniques described herein can also be used to improve the accuracy of the measured masses of proteomics data.

As a result, in various embodiments, nominal or non-accurate mass product ion spectral libraries are converted automatically to accurate mass product ion spectral libraries using a computer so that when unknown accurate mass spectra are compared to such libraries the lowest common denominator is an accurate mass value. Such a conversion can be referred to as in-silico meaning that the conversion is performed in or by a computer or processor.

In various embodiments, at least three pieces of information are used in the conversion. A first piece of information is the compound structure itself. A second piece of information is the data in the existing spectral repositories, which includes data collection conditions (such as polarity, Q1 resolution and collision energy). A third piece of information is one or more experiment-tailored in-silico fragmentation rules for a parent compound structure. For example, m/z values in a spectral repository are adjusted (while keeping the relative fragment intensities) to convert them to an accurate mass counterpart that would have been collected under the same ionization and CID conditions using an accurate mass instrument.

In various embodiments, to successfully convert mass spectra into accurate mass ones, complementary information in the spectral repository is leveraged, if available. This can be done by storing a putative spectral fragment and neutral loss annotation with the supporting information (such as m/z error, score, rings plus double bonds (RDB), hydrogen migration, or type of broken bonds).

In various embodiments, in order to resolve predicted fragments that are isobaric, or have the same mass within the accuracy of the low accuracy data or library spectrum, scoring of the likelihood of the fragment is used to filter out entries that are less likely. Existing fragment scoring (based on m/z error, odd/even electrons, number and type of broken bonds to yield fragment, hydrogen migration) is expanded in at least four different ways.

(i) Use the evidence from cascading fragments to score and filter isobaric fragments (i.e., can the fragment existence be explained through a difference of common neutral loss in terms of a preceding fragment).

Figure 3:
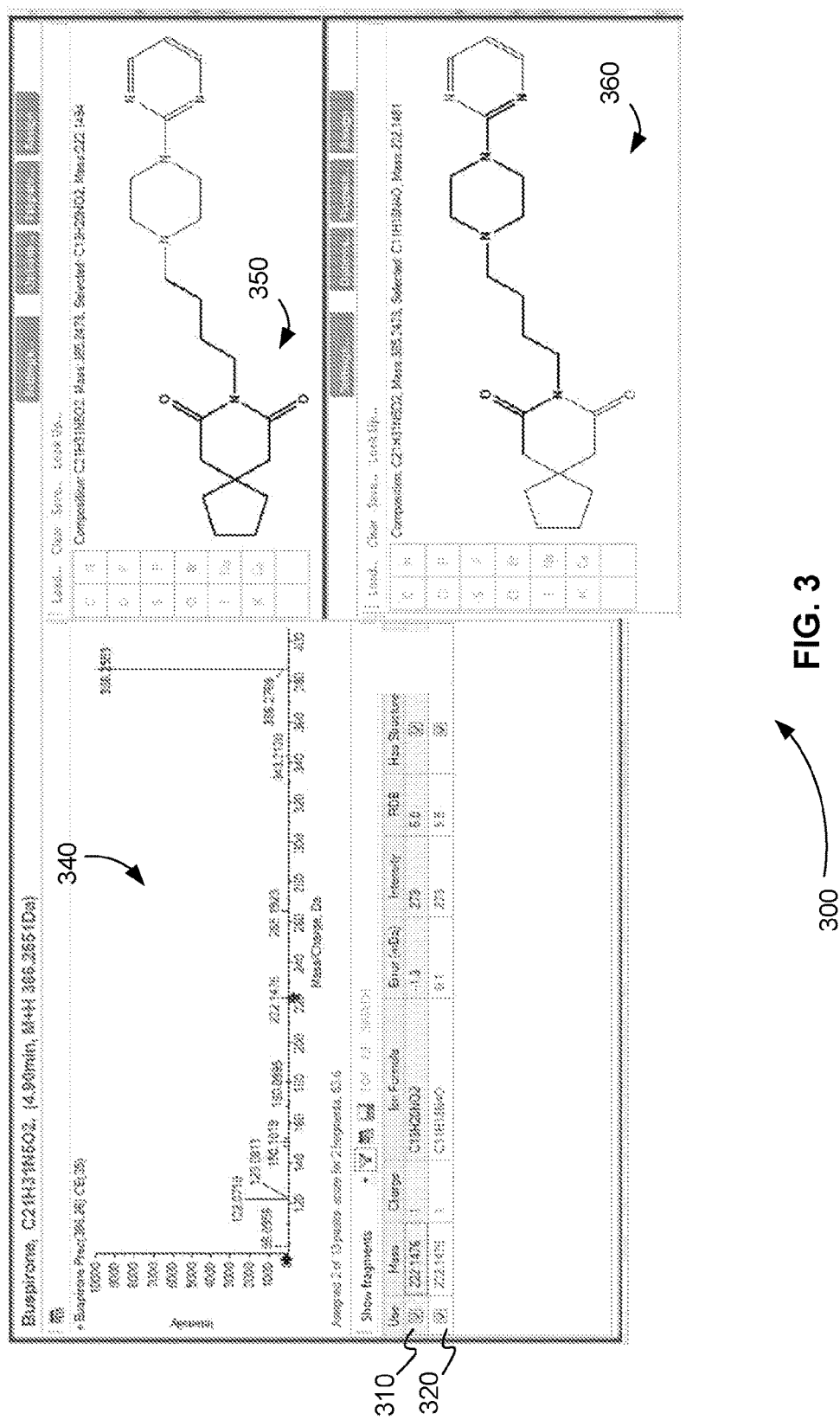
FIG. 3 is an exemplary screen capture of information from a display window of a fragmentation evaluation tool showing isobaric fragments, in accordance with various embodiments.

FIG. 3 is an exemplary screen capture 300 of information from a display window of a fragmentation evaluation tool showing isobaric fragments, in accordance with various embodiments. Screen capture 300 shows two high scoring isobaric predicted fragments 310 and 320 for buspirone. Screen capture 300 also shows a product ion spectrum 340 for buspirone, a chemical structure for buspirone with substructure 350 of fragment 310 highlighted, and a chemical structure for buspirone with substructure 360 of fragment 320 highlighted. The exact masses of fragments 310 and 320 correspond to a measured mass of 222.1476 within 0.002 amu.

Figure 4:
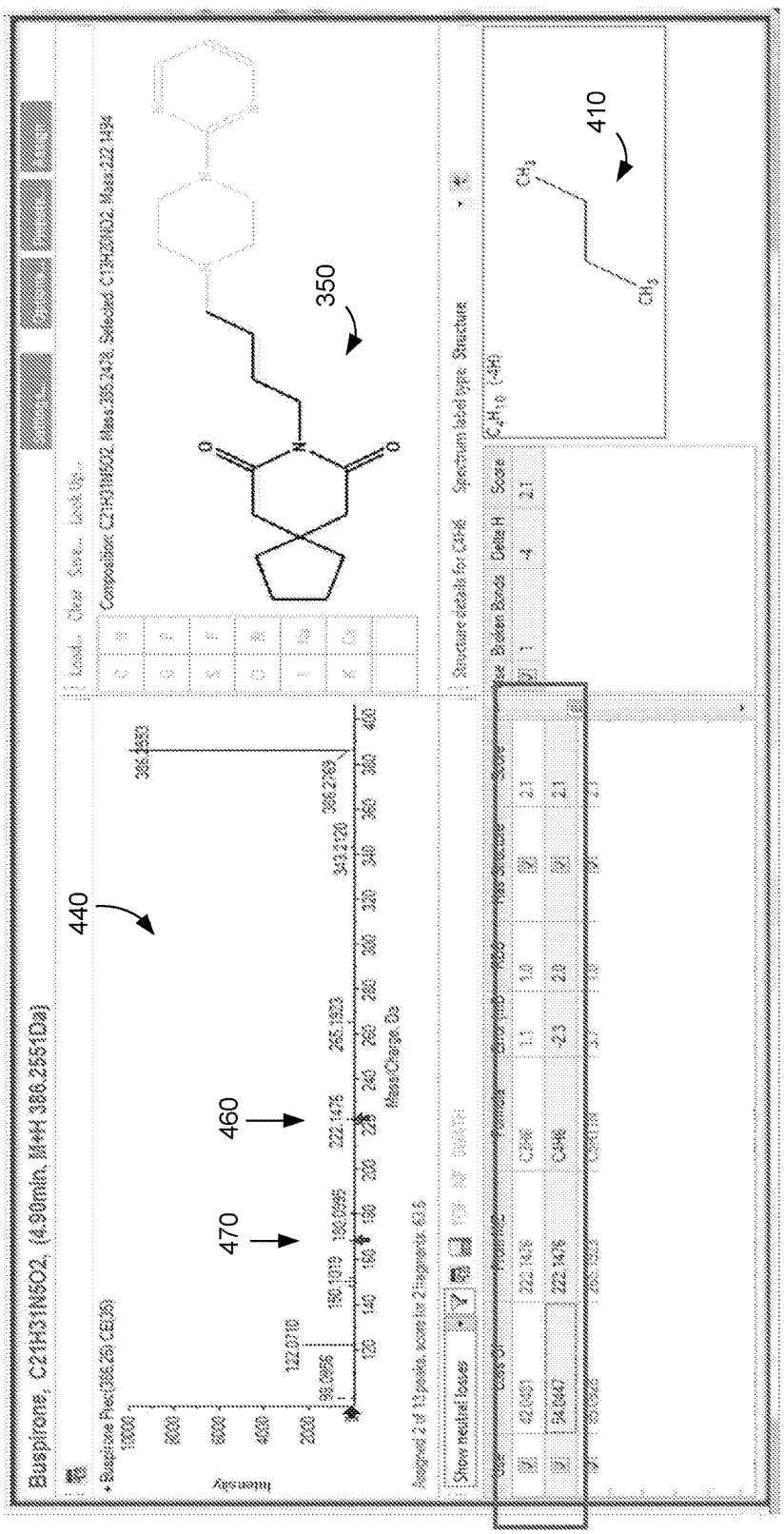
FIG. 4 is an exemplary screen capture of information from a display window of a fragmentation evaluation tool showing cascading neutral losses, in accordance with various embodiments.

FIG. 4 is an exemplary screen capture 400 of information from a display window of a fragmentation evaluation tool showing cascading neutral losses, in accordance with various embodiments. Screen capture 400 shows that a fragment's existence can be explained through a difference of common neutral loss. In other words, by tracking information from potential cascading neutral losses, and their contributions to fragment scores, unlikely isobaric fragment assignments can be filtered out.

For example, screen capture 400 shows product ion spectrum 440 and a chemical structure for buspirone with substructure 350 of FIG. 3 highlighted. Neutral loss 410 has a loss of 54.0447 Da from peak 460 to peak 470 in product ion spectrum 440. Since substructure 350 of FIG. 3 can include neutral loss 410. Fragment 310 of FIG. 3 is more likely than fragment 320 of Figure. Thus, FIGS. 3 and 4 show how isobaric fragments can be scored and filtered using neutral loss information.

(ii) Use fragment stability to score and filter isobaric fragments (the type of certain broken bonds to yield a fragment is less energetically demanding than others).

Figure 5:
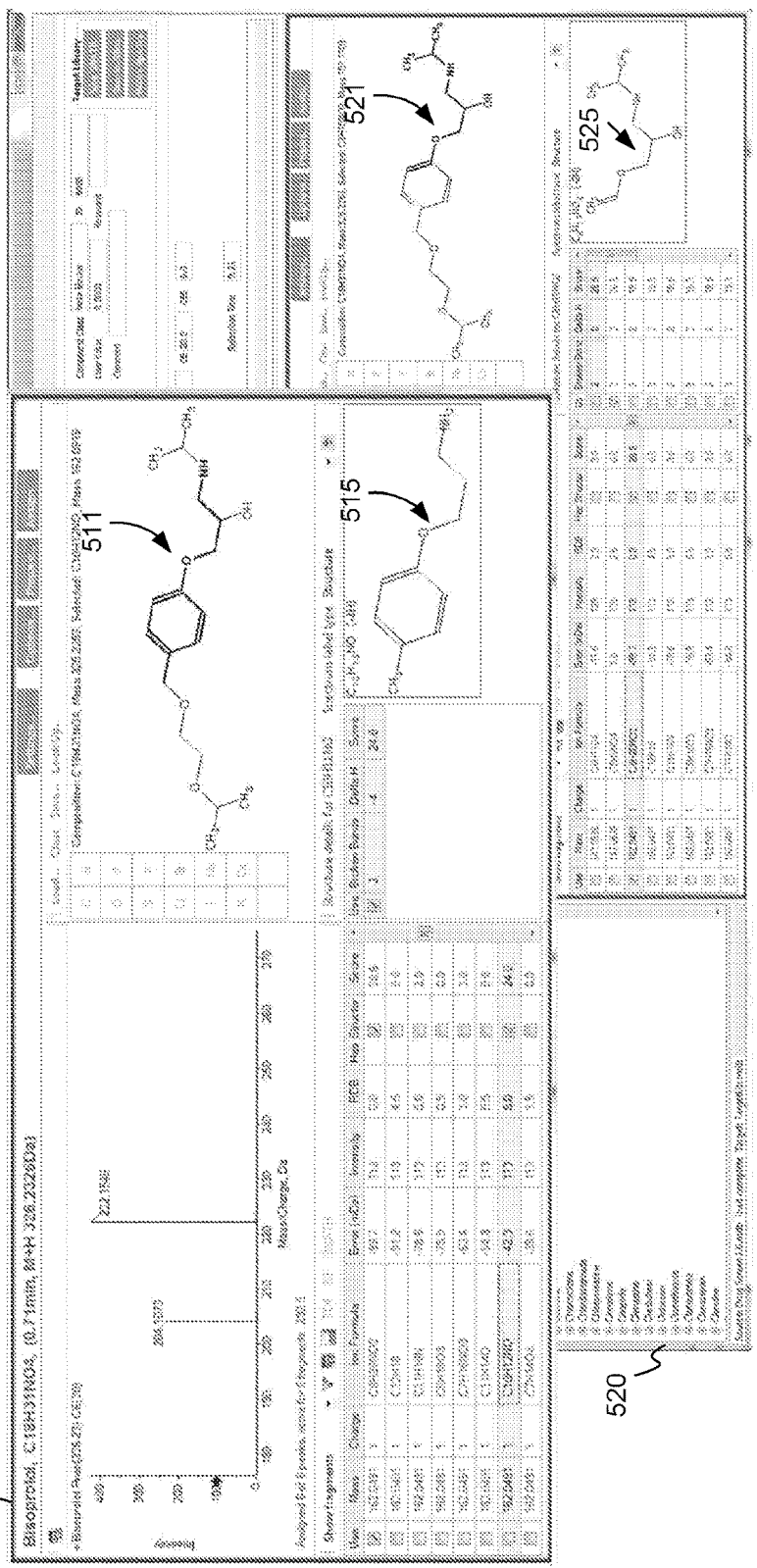
FIG. 5 is an exemplary screen capture of information from two overlaid display windows of a fragmentation evaluation tool showing fragments resulting from two different types of broken bonds, in accordance with various embodiments.

FIG. 5 is an exemplary screen capture 500 of information from two overlaid display windows of a fragmentation evaluation tool showing fragments resulting from two different types of broken bonds, in accordance with various embodiments. Display window 510 and display window 520 both display the chemical structure for bisoprolol 511 and 521, respectively. However, display window 510 shows the chemical structure of a fragment of bisoprolol 515 that results from 3 C-heteroatom bonds being broken. In contrast, display window 520 shows the chemical structure of a fragment of bisoprolol 525 that results from 2 aromatic bonds being broken. Although fewer bonds need to be broken to produce structure 525 as compared to structure 515, structure 525 is actually less likely. This is because aromatic ring bonds are much more stable than C-heteroatom bonds.

Figure 6:
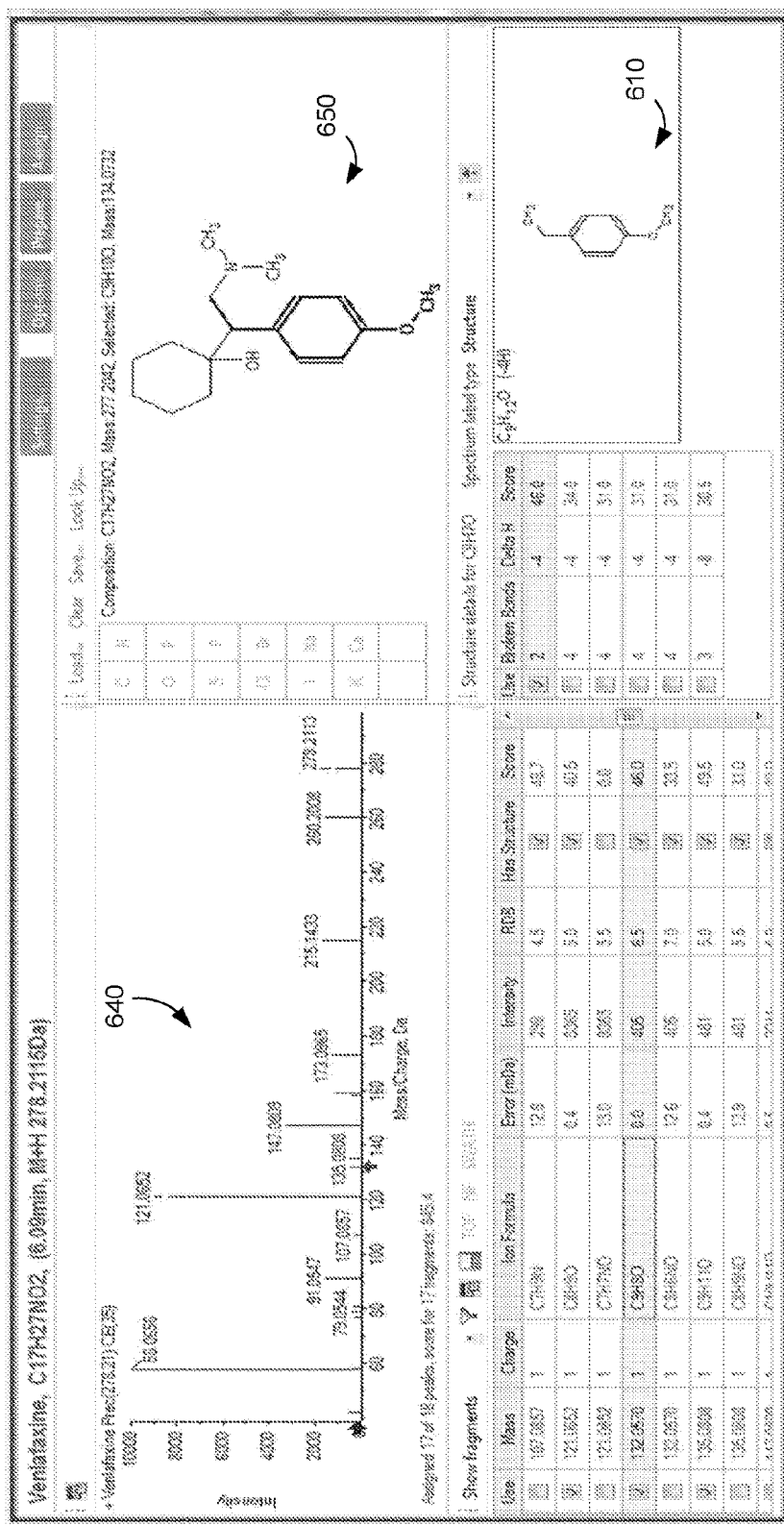
FIG. 6 is an exemplary screen capture of information from a display window of a fragmentation evaluation tool showing the chemical structure of a fragment of venlafaxine, in accordance with various embodiments.

FIG. 6 is an exemplary screen capture 600 of information from a display window of a fragmentation evaluation tool showing the chemical structure of a fragment of venlafaxine, in accordance with various embodiments. Screen capture 600 shows the chemical structure of fragment of venlafaxine 610 that has a mass of 132.0570. Screen capture 600 also shows a product ion spectrum 640 and a chemical structure 650 for venlafaxine.

Figure 7:
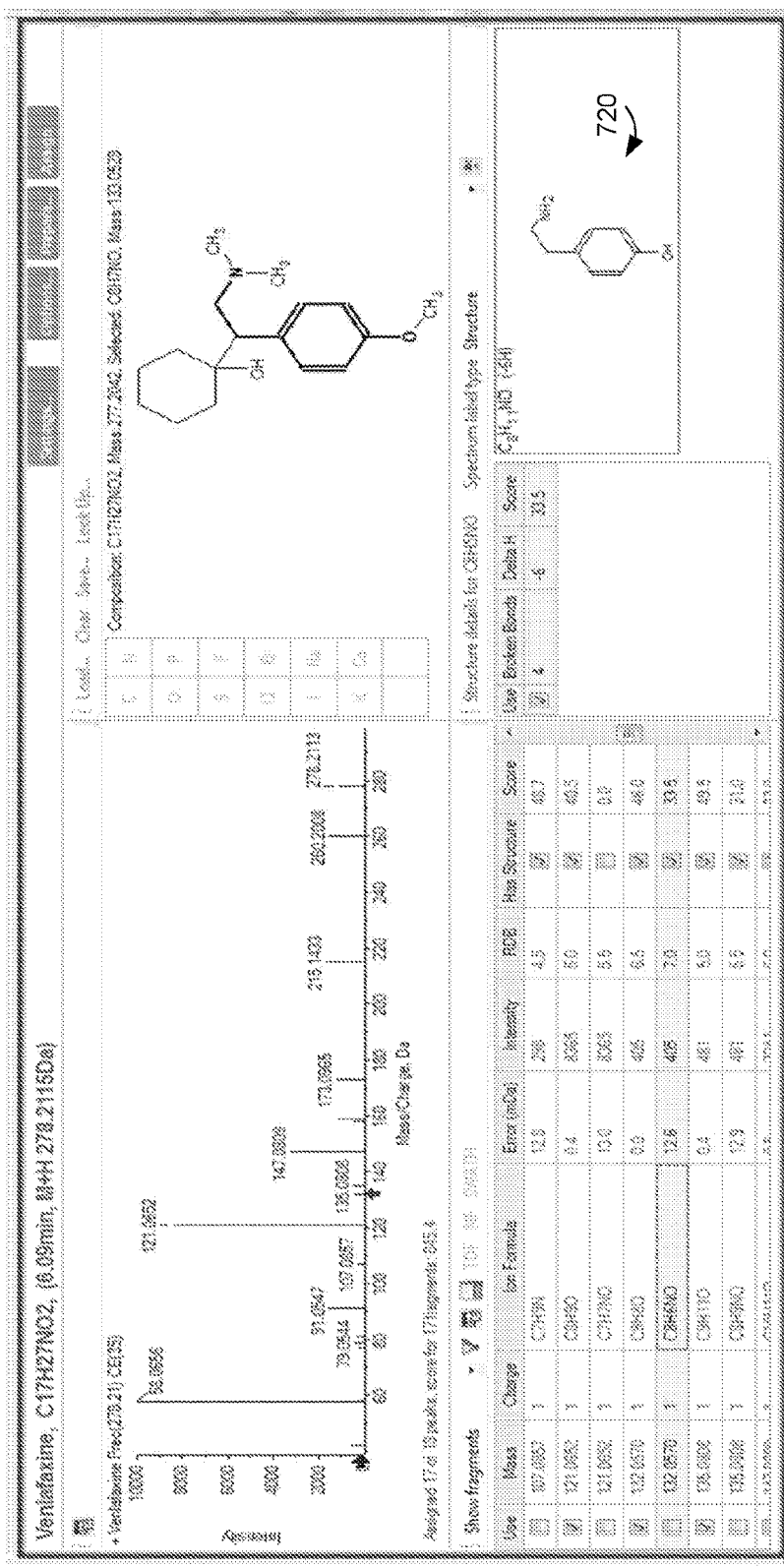
FIG. 7 is an exemplary screen capture of information from a display window of a fragmentation evaluation tool showing the chemical structures of another fragment of venlafaxine that also has a mass of 132.0570, in accordance with various embodiments.

FIG. 7 is an exemplary screen capture 700 of information from a display window of a fragmentation evaluation tool showing the chemical structures of another fragment of venlafaxine that also has a mass of 132.0570, in accordance with various embodiments. Screen capture 700 shows the chemical structure of fragment 720 of venlafaxine that has a mass of 132.0570.

Fragment structures 610 of FIGS. 6 and 720 of FIG. 7 are isobaric fragments of venlafaxine. Structure 610 of FIG. 6 is more stable and is, therefore, more likely, because it is much easier to break C—N bonds than C—C bonds. In other words, structure 720 of FIG. 7 includes a penalty for containing a C—N bond that is not broken and is, therefore, less likely.

(iii) Use fragmentation rules based on the CID conditions to score and filter isobaric fragments (such as breaking of aromatic bonds is unlikely at low CE). See also FIGS. 5-7.

(iv) Where possible, use fragment evidence from the chemical space studied and searched for a given substructure in the spectral repository and corresponding experimental data and their assignment to score and filter isobaric fragments.

The chemical space of zepam compounds includes 7-aminoclonazepam, diazepam, and temazepam, for example. All of the zepam compounds have a fragment at 193 Da. In order to determine the fragment at 193 Da the fragments of 7-aminoclonazepam, diazepam, and temazepam, at or around 193 Da are compared.

Figure 8:
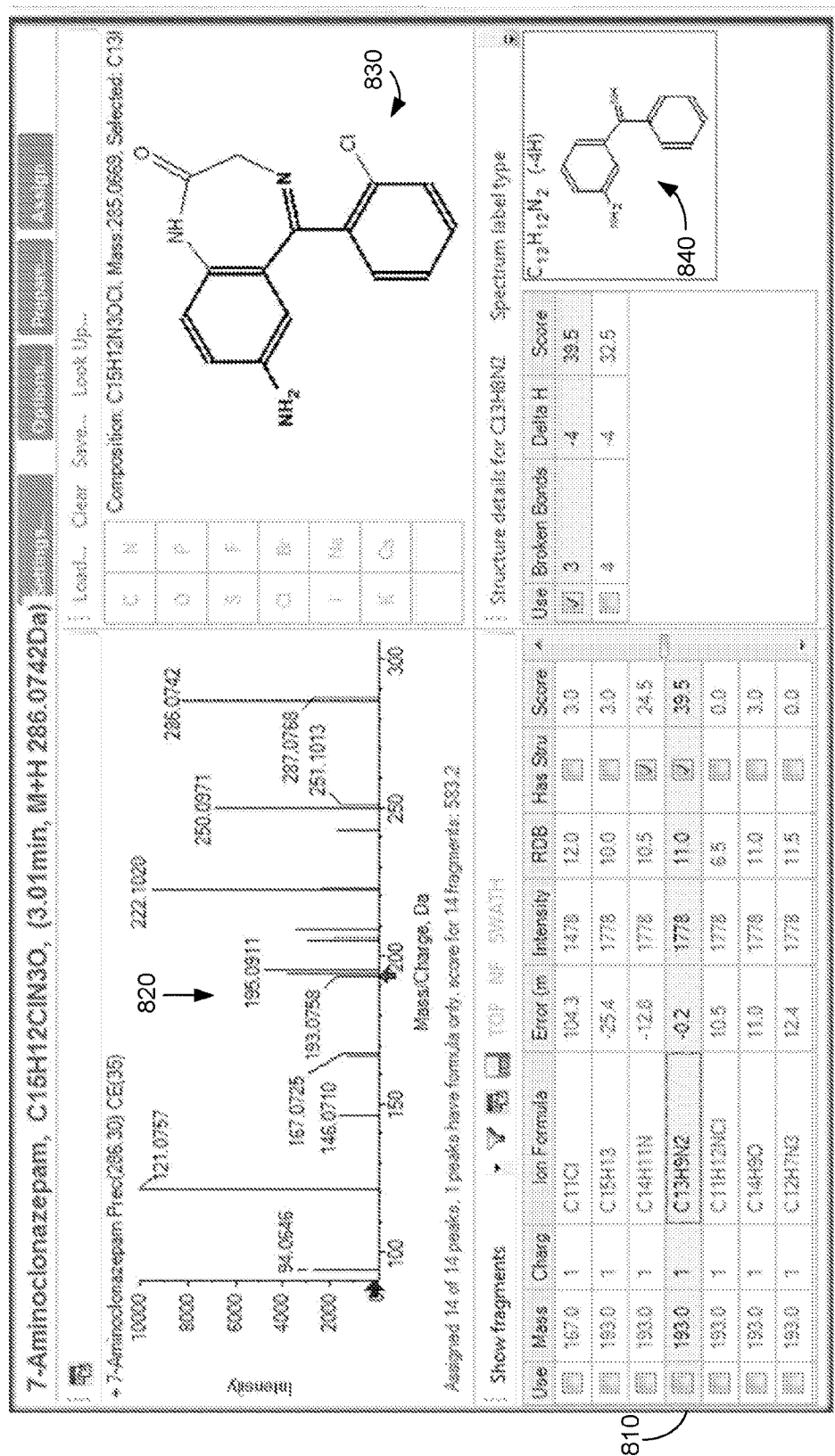
FIG. 8 is an exemplary screen capture of information from a display window of a fragmentation evaluation tool showing the chemical structure of a fragment of 7-aminoclonazepam having a nominal mass of 193 and having the highest score, in accordance with various embodiments.

FIG. 8 is an exemplary screen capture 800 of information from a display window of a fragmentation evaluation tool showing the chemical structure of a fragment of 7-aminoclonazepam having a nominal mass of 193 and having the highest score, in accordance with various embodiments. Screen capture 800 shows highest scoring fragment 810 ($C_{13}H_9N_2$) for 7-aminoclonazepam having an m/z of 193 Da. Screen capture 800 also shows a product ion spectrum 820 for 7-aminoclonazepam, a chemical structure 830 for 7-aminoclonazepam, and a fragment substructure 840 for fragment 810 of 7-aminoclonazepam.

Figure 9:
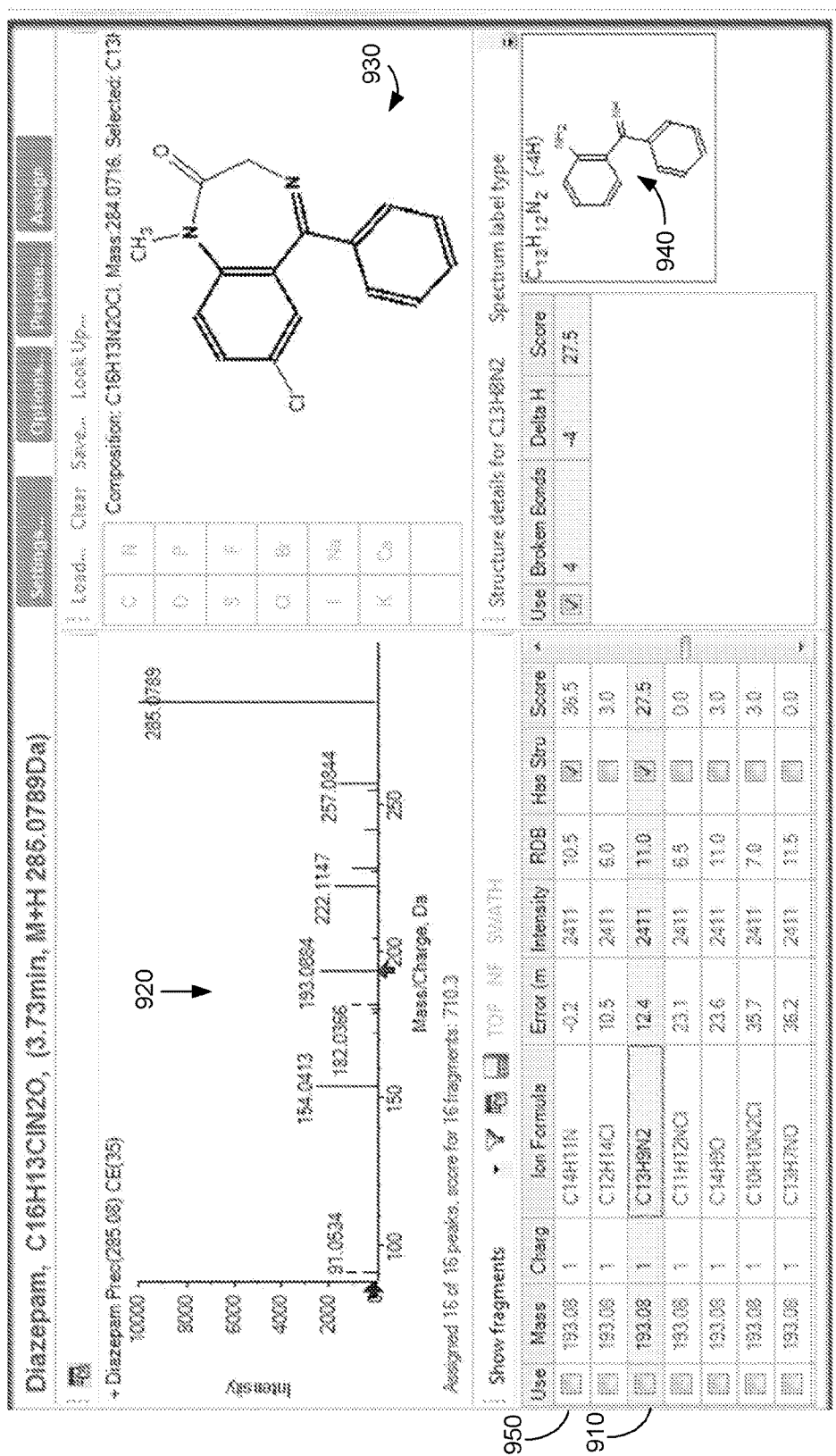
FIG. 9 is an exemplary screen capture of information from a display window of a fragmentation evaluation tool showing the chemical structure of a fragment of diazepam having a similar structure as the highest scoring fragment in FIG. 8, in accordance with various embodiments.

FIG. 9 is an exemplary screen capture 900 of information from a display window of a fragmentation evaluation tool showing the chemical structure of a fragment of diazepam having a similar structure as the highest scoring fragment in FIG. 8, in accordance with various embodiments. Screen capture 900 shows fragment 910 ($C_{13}H_9N_2$) for diazepam having an m/z of 193 Da. Screen capture 900 shows a product ion spectrum 920 for diazepam, a chemical structure 930 for diazepam, and a fragment substructure 940 for fragment 910 of diazepam. Screen capture 900 also shows fragment 950 ($C_{14}H_{11}N$), which has a higher score than fragment 910 ($C_{13}H_9N_2$).

Figure 10:
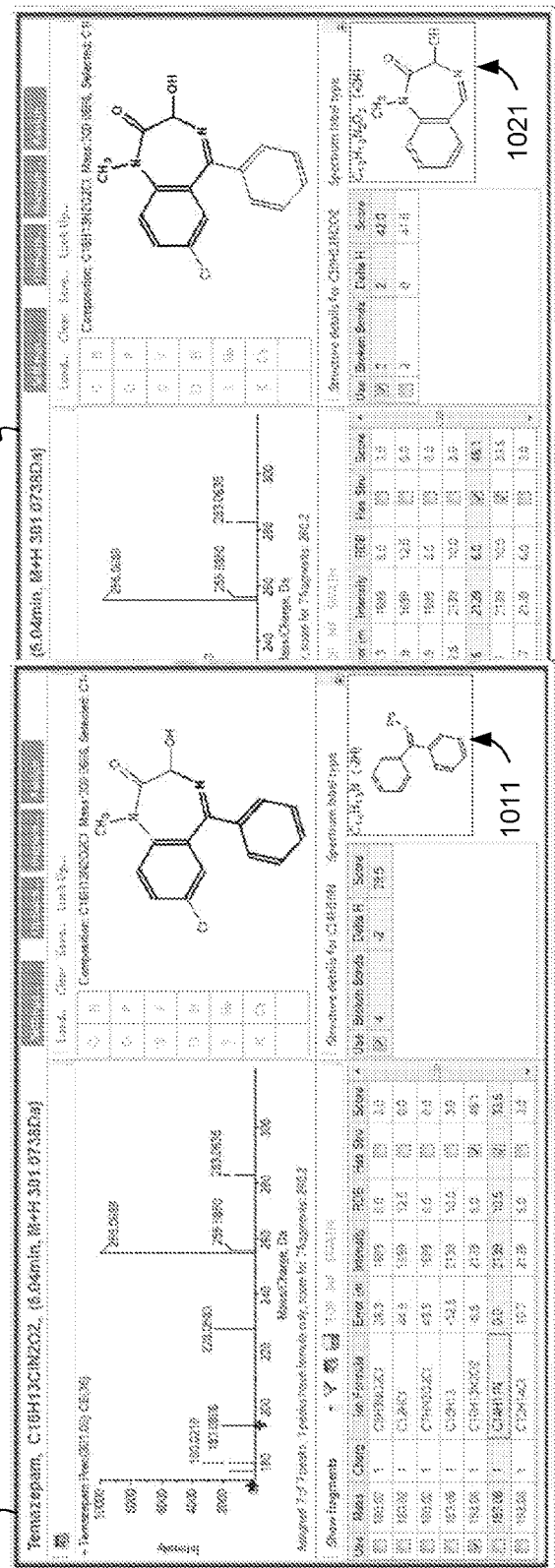
FIG. 10 is an exemplary screen capture of information from two overlaid display windows of a fragmentation evaluation tool showing the chemical structures of two fragments of temazepam that also have a mass of 193, in accordance with various embodiments.

FIG. 10 is an exemplary screen capture 1000 of information from two overlaid display windows of a fragmentation evaluation tool showing the chemical structures of two fragments of temazepam that also have a nominal mass of 193, in accordance with various embodiments. Display window 1010 shows the chemical structure of fragment 1011 ($C_{13}H_9N_2$) of temazepam. Display window 1020 shows the chemical structure of a different fragment 1021 ($C_{10}H_{13}N_2O_2$) of temazepam.

FIGS. 8-10 show that the chemical structures of 7-aminoclonazepam, diazepam, and temazepam are very similar to one another. In addition, the spectra of all three compounds have a fragment at m/z 193.08. For consistency it makes sense that the structure of this fragment should be the same—or at least very similar—in all four cases. Looking at FIG. 8, the overall highest scoring fragment for 7-aminoclonazepam is fragment 810 ($C_{13}H_9N_2$). So if it is assumed that this is the correct assignment for this molecule, the correct assignment for diazepam in FIG. 8 should be the analogous one, i.e., fragment 910 ($C_{13}H_9N_2$) even though fragment 950 ($C_{14}H_{11}N$) has a higher score.

FIG. 10 shows the selection of the correct fragment more clearly. Fragment 1021 is probably NOT correct, because its chemical structure is not very similar to chemical structures 840 and 940 of FIGS. 8 and 9, respectively, the presumed correct fragments. For example, fragment 1021 of FIG. 10 does not have the benzene ring at the "bottom" of the structure, which chemical structures 840 and 940 of FIGS. 8 and 9 have. Fragment 1011 of FIG. 10, however, is similar to the chemical structures 840 and 940 of FIGS. 8 and 9, and is, therefore, more likely to be correct.

In various embodiments, when no one unique fragment or composition can be assigned to a given fragment (i.e., two possibilities have a similar score), the fragment can be annotated with multiple possibilities.

In various embodiments, fragments are annotated with the elemental compositions and any potential substructure pieces. Elemental compositions with a high score but without substructures are retained to allow for unanticipated fragmentation, such as rearrangements.

In various embodiments, once the correct element compositions are assigned to the peaks in the MS/MS or product ion spectra, the spectra collected with approximately unit Q1 resolution are converted into non-specific fragmentation spectra by injecting a theoretical isotope pattern for each annotated fragment into the spectra.

Figure 11:
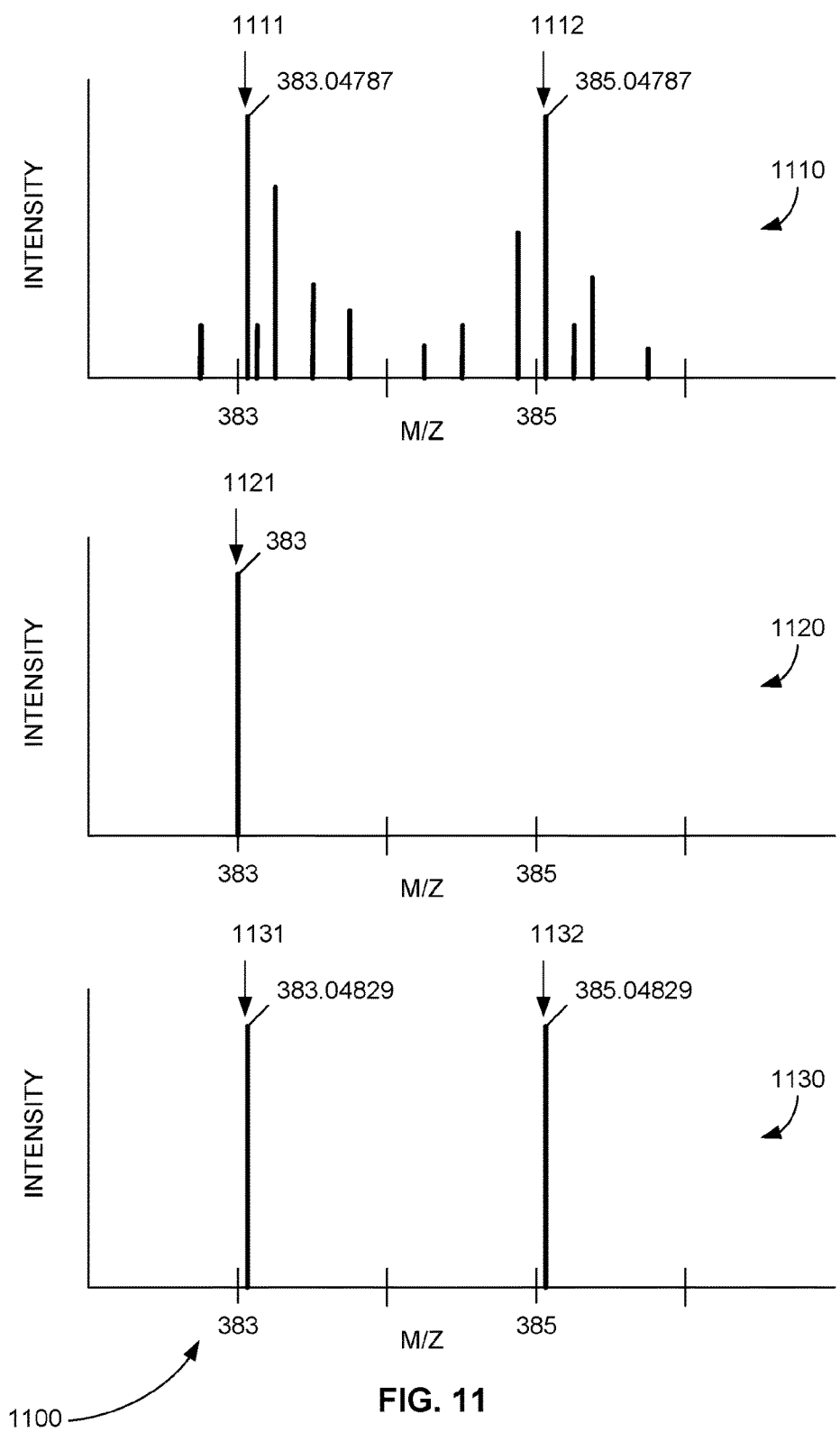
FIG. 11 is an exemplary series of mass spectrum plots showing how spectra are converted into accurate non-specific fragmentation spectra by injecting a theoretical isotope pattern for each annotated fragment into the spectra, in accordance with various embodiments.

FIG. 11 is an exemplary series of mass spectrum plots 1100 showing how spectra are converted into accurate non-specific fragmentation spectra by injecting a theoretical isotope pattern for each annotated fragment into the spectra, in accordance with various embodiments. Plot 1110 shows a portion of an exemplary non-specific fragmentation spectrum produced from an accurate experimental non-specific fragmentation method. Because a non-specific fragmentation method was used, the fragments or product ions have a full isotopic pattern. This would not be the case if a narrow precursor ion window or narrow Q1 window had been used. The compound in plot 1120 has a bromine atom, which has a distinctive isotope pattern. The pattern includes two isotopes of roughly equal intensity separated by 2 Da. The two isotopes are shown in FIG. 11 as peaks 1111 and 1112. A typical product ion spectrum acquired with a narrow precursor window would only show one of these isotopes.

Plot 1120 shows a portion of an exemplary library spectrum. The spectrum shows a low accuracy mass of 383 for a fragment of the known compound. The spectrum of plot 1120 was acquired with a narrow precursor ion window. As a result, the spectrum of plot 1120 shows only one isotope peak 1121 for the known compound.

In various embodiments, during the conversion of nominal or lower-accuracy mass library spectra to accurate mass library spectra, theoretical or processor generated isotope masses are added back to the high accuracy mass library spectra.

Plot 1130 shows a portion of an exemplary converted accurate mass library spectrum. Comparing plot 1120 and 1130 shows that mass peak 1121 of the mass library spectrum in plot 1120 was converted to accurate mass peak 1131 in accurate mass library spectrum in plot 1130. In addition, theoretical isotope mass peak 1132 was added to the high accuracy mass library spectrum in plot 1130.

Accurate mass library spectrum in plot 1130 can then be used, for example, to determine if the known compound is in any non-specific fragmentation spectrum, such as the one shown in plot 1110. For example, the non-specific fragmentation spectrum of plot 1110 is searched against the high accuracy mass library spectrum in plot 1130.

System for Converting Product Ion Mass Spectra

Various embodiments include a system for converting product ion mass spectra to product ion mass spectra with higher mass accuracy, in accordance with various embodiments. This system includes a processor configured to process tandem mass spectrometry data post-acquisition. The processor can be, but is not limited to, a computer, microprocessor, the computer system of FIG. 1, the processor of FIG. 2 or any device capable of processing data and sending and receiving data.

The processor receives at least one product ion mass spectrum produced by a tandem mass spectrometer. The tandem mass spectrometer is, for example, a low accuracy tandem mass spectrometer. The processor receives the at least one product ion mass spectrum from a low accuracy spectral library, for example.

Figure 12:
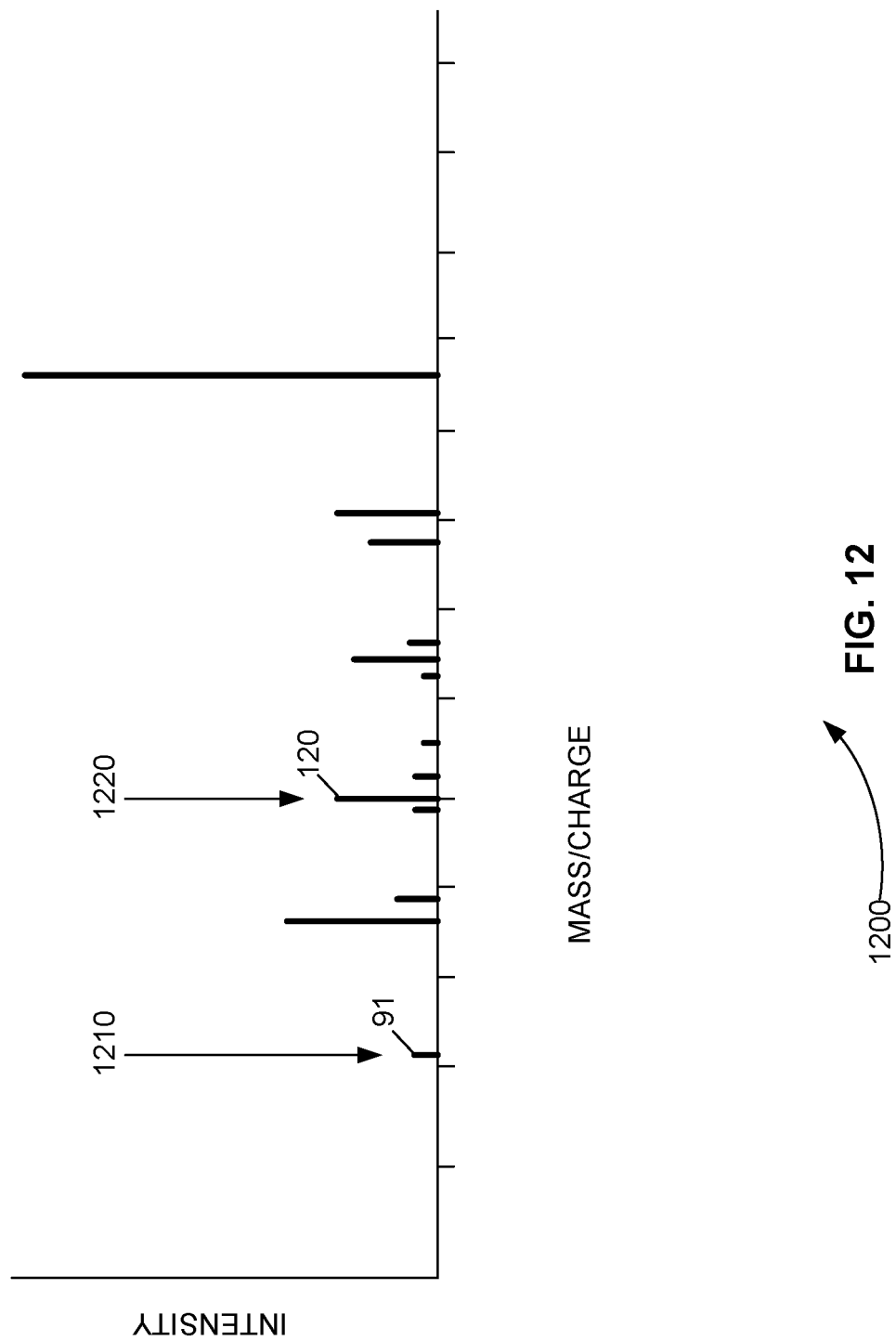
FIG. 12 is an exemplary nominal or low-accuracy product ion mass spectrum for epinephrine, in accordance with various embodiments.

FIG. 12 is an exemplary nominal or low-accuracy product ion mass spectrum 1200 for epinephrine, in accordance with various embodiments. Product ion mass spectrum 1200 includes peaks 1210 and 1220 that have masses of 91 and 120 Da, respectively.

In addition to the at least one product ion mass spectrum, the processor receives a chemical structure of a compound that corresponds to the at least one product ion mass spectrum. In various embodiments the chemical structure of a compound that corresponds to the at least one product ion mass spectrum is also received from a spectral library. In other embodiments, the chemical structure may be received from another library or database.

The processor assigns one or more elemental compositions to at least one peak in the at least one product ion spectrum based on the chemical structure. The processor selects at least one elemental composition of the one or more assigned elemental compositions for the at least one peak. Finally, the processor converts the mass of the at least one peak to the mass of the selected at least one elemental composition, producing a product ion mass spectrum with higher mass accuracy.

Figure 13:
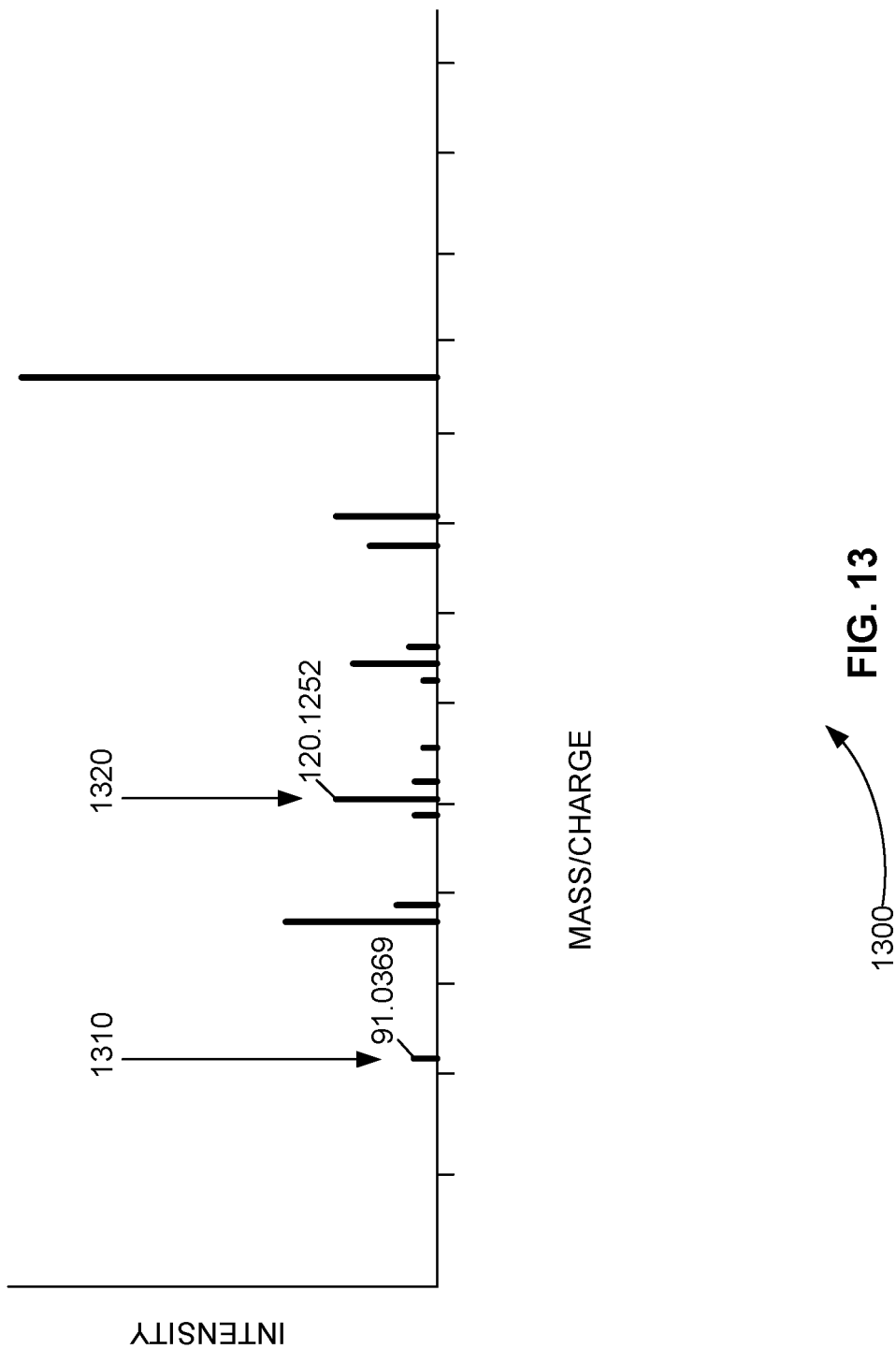
FIG. 13 is an exemplary converted accurate product ion mass spectrum for epinephrine, in accordance with various embodiments.

FIG. 13 is an exemplary converted accurate product ion mass spectrum 1300 for epinephrine, in accordance with various embodiments. Converted accurate product ion mass spectrum 1300 includes peaks 1310 and 1320 that have accurate masses of 91.0369 and 120.1252 Da, respectively.

As described above, the processor can assign and select elemental compositions in a variety of ways. In various embodiments, the processor assigns one or more elemental compositions to the at least one peak in the at least one product ion spectrum by simulating one or more fragmentations of the chemical structure that produce one or more substructures of the chemical structure, and assigning to the at least one peak elemental compositions of the one or more substructures that have a mass within a mass tolerance of the mass of the at least one peak. The processor then selects at least one elemental composition by scoring the one or more assigned elemental compositions and selecting at least one elemental composition with the highest score, for example. The scoring can be based on fragmentation rules.

In an alternative embodiment, the processor assigns one or more elemental compositions to the at least one peak in the at least one product ion spectrum by calculating one or more elemental compositions from the elements of the chemical structure that have masses within a mass tolerance of the mass of the at least one peak, and assigning the one or more elemental compositions to the at least one peak. At least one elemental composition can be selected in a number of ways.

In various embodiments, the processor selects at least one elemental composition by scoring the one or more assigned elemental compositions, and selecting at least one elemental composition with the highest score. The one or more assigned elemental compositions are scored, for example, based on a mass difference between at least one elemental composition and the mass of the at least one peak.

In various embodiments, the processor selects at least one elemental composition based on two scores. As noted above, the processor selects at least one elemental composition by scoring the one or more assigned elemental compositions. In addition, the processor simulates one or more fragmentations of the chemical structure that produce one or more substructures of the chemical structure, assigns to the at least one peak one or more substructures that have a mass within a mass tolerance of the mass of the at least one peak, and scores the one or more substructures. The processor finally combines the scores of assigned substructures and their corresponding elemental compositions, and selects a corresponding elemental composition of an assigned substructure that has the highest combined score.

In various embodiments, the one or more assigned elemental compositions are scored based on a mass difference between at least one elemental composition and the mass of the at least one peak, and the one or more substructures are scored based on fragmentation rules.

In various embodiments, the processor further receives at least one data collection condition that corresponds to the at least one product ion mass spectrum. The collection condition is used by a fragmentation rule during scoring, for example. The collection condition can include, but is not limited to, one or more of a polarity, a first quadrupole Q1 resolution, a precursor mass-to-charge ratio (m/z), an m/z error distribution, a target product ion spectrum Q1 width, and a collision energy.

In various embodiments, after the processor converts the mass of the at least one peak to the mass of the selected at least one elemental composition, the processor further adds one or more isotopic peaks of the at least one peak to the product ion mass spectrum with higher mass accuracy.

In various alternative embodiments, the processor adds one or more isotopic peaks of the at least one peak to the product ion mass spectrum with higher mass accuracy without converting the mass of the at least one peak to the mass of the selected at least one elemental composition. In other words, the processor receives at least one product ion mass spectrum produced by a tandem mass spectrometer. The processor receives a chemical structure of a compound that corresponds to the at least one product ion mass spectrum. The processor assigns one or more elemental compositions to at least one peak in the at least one product ion spectrum based on the chemical structure. The processor selects at least one elemental composition of the one or more assigned elemental compositions for the at least one peak. However, instead of converting the mass of the at least one peak to the mass of the selected at least one elemental composition, the processor adds one or more isotopic peaks of the at least one peak to the product ion mass spectrum, producing a product ion mass spectrum suitable for use with a non-specific precursor ion selection method.

In various embodiments, a mass tolerance is a known error range of the lower accuracy mass measured by the tandem mass spectrometer.

Method for Converting Product Ion Mass Spectra

Figure 14:
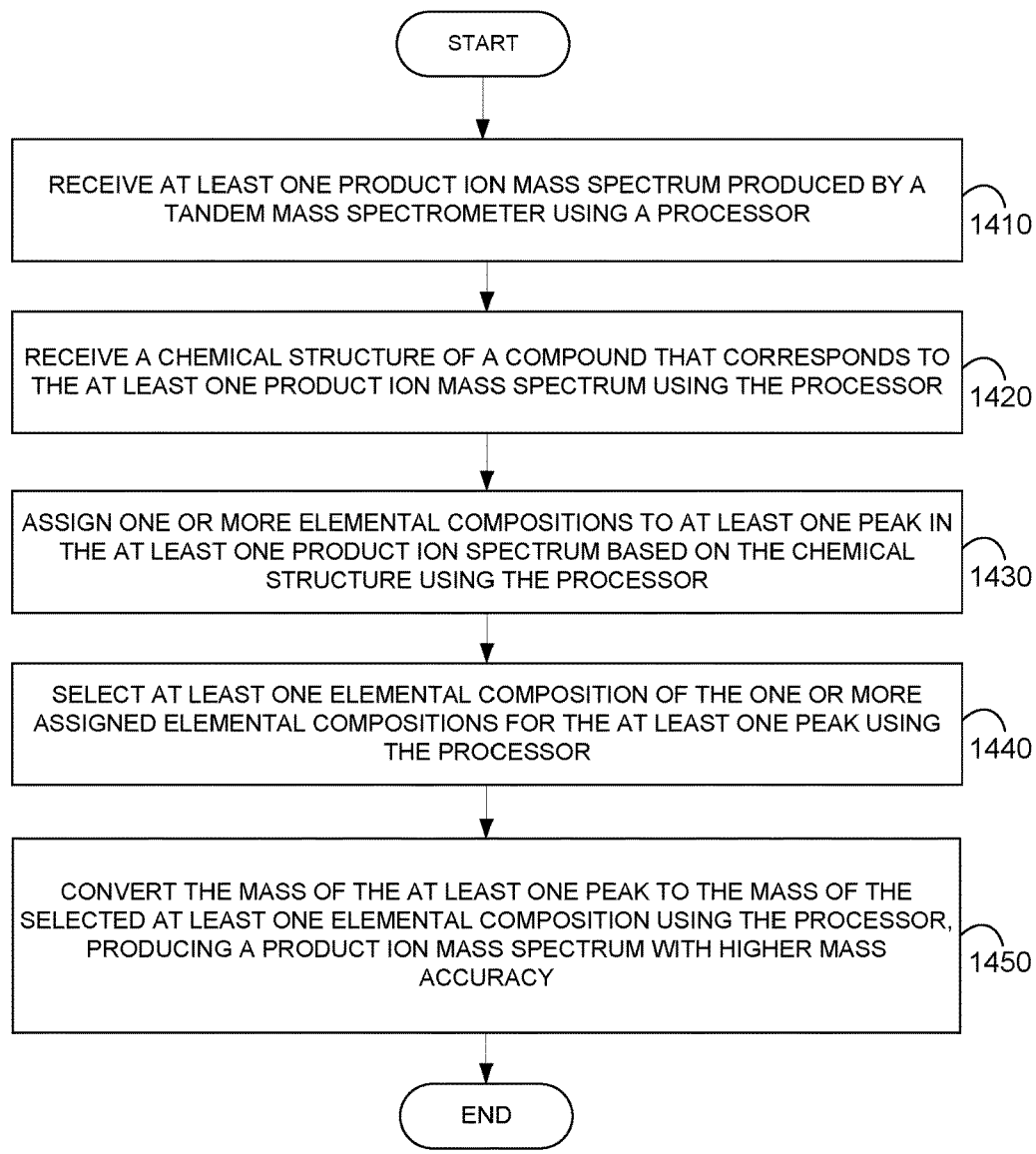
FIG. 14 is a flowchart showing a method for converting product ion mass spectra to product ion mass spectra with higher mass accuracy, in accordance with various embodiments.

FIG. 14 is a flowchart showing a method 1400 for converting product ion mass spectra to product ion mass spectra with higher mass accuracy, in accordance with various embodiments.

In step 1410 of method 1400, at least one product ion mass spectrum produced by a tandem mass spectrometer is received using a processor.

In step 1420, a chemical structure of a compound that corresponds to the at least one product ion mass spectrum is received using the processor.

In step 1430, one or more elemental compositions are assigned to at least one peak in the at least one product ion spectrum based on the chemical structure using the processor.

In step 1440, at least one elemental composition of the one or more assigned elemental compositions is selected for the at least one peak using the processor.

In step 1450, the mass of the at least one peak is converted to the mass of the selected at least one elemental composition using the processor, producing a product ion mass spectrum with higher mass accuracy.

Computer Program Product for Converting Product Ion Mass Spectra

In various embodiments, computer program products include a tangible computer-readable storage medium whose contents include a program with instructions being executed on a processor so as to perform a method for converting product ion mass spectra to product ion mass spectra with higher mass accuracy. This method is performed by a system that includes one or more distinct software modules.

Figure 15:
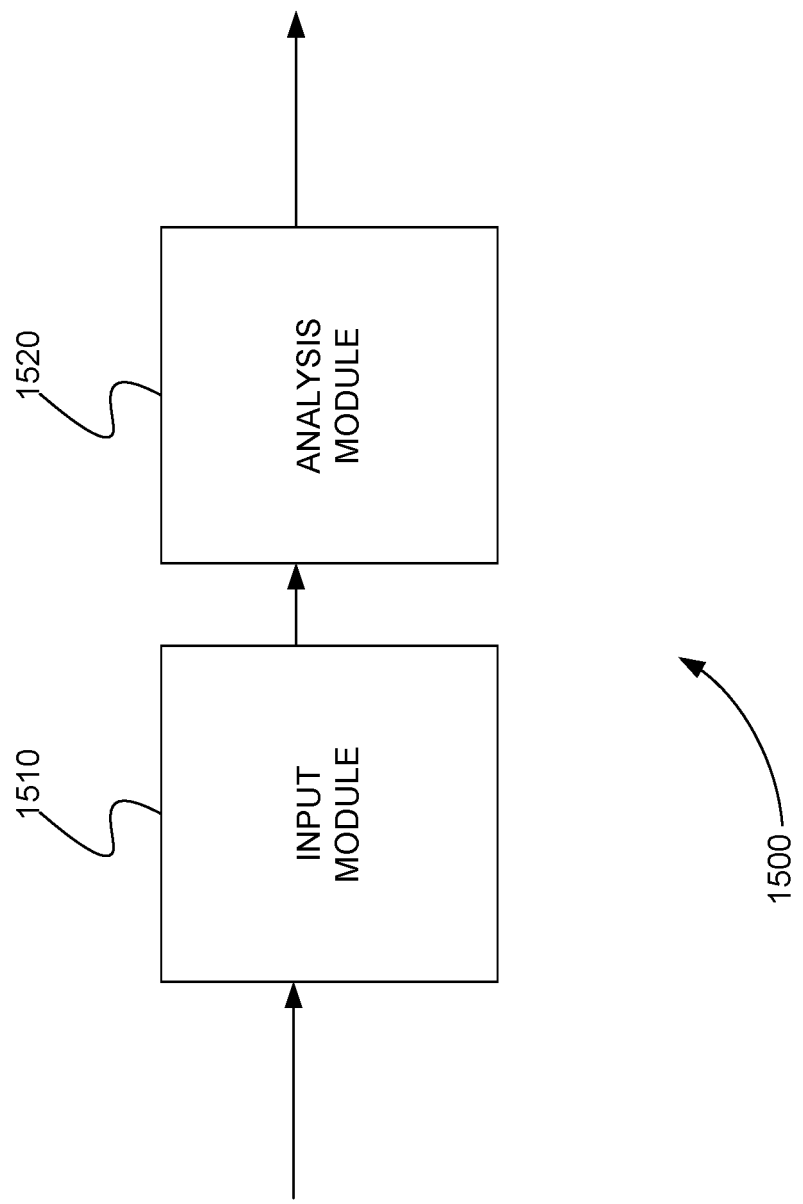
FIG. 15 is a schematic diagram of a system that includes one or more distinct software modules that performs a method for converting product ion mass spectra to product ion mass spectra with higher mass accuracy, in accordance with various embodiments.

FIG. 15 is a schematic diagram of a system 1500 that includes one or more distinct software modules that performs a method for converting product ion mass spectra to product ion mass spectra with higher mass accuracy, in accordance with various embodiments. System 1500 includes input module 1510 and analysis module 1520.

Input module 1510 module receives at least one product ion mass spectrum produced by a tandem mass spectrometer. Input module 1510 receives a chemical structure of a compound that corresponds to the at least one product ion mass spectrum.

Analysis module 1520 assigns assigning one or more elemental compositions to at least one peak in the at least one product ion spectrum based on the chemical structure. Analysis module 1520 selects at least one elemental composition of the one or more assigned elemental compositions for the at least one peak using the analysis module. Finally, analysis module 1520 converts the mass of the at least one peak to the mass of the selected at least one elemental composition using the analysis module, producing a product ion mass spectrum with higher mass accuracy.

One of ordinary skill in the art can appreciate that the use of the term "mass" used herein with regard to mass spectrometry data is interchangeable with the term "mass-to-charge ratio (m/z)".

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

What is claimed is:

1. A system for converting product ion mass spectra to product ion mass spectra with higher mass accuracy, comprising:
    a processor that
        receives at least one product ion mass spectrum produced by a tandem mass spectrometer,
        receives a chemical structure of a compound that corresponds to the at least one product ion mass spectrum,
        assigns one or more elemental compositions to at least one peak in the at least one product ion spectrum based on the chemical structure by calculating one or more elemental compositions from the elements of the chemical structure that have masses within a mass tolerance of the mass of the at least one peak and assigning the one or more elemental compositions to the at least one peak,
        scores the one or more assigned elemental compositions,
        simulates one or more fragmentations of the chemical structure to produce a plurality of substructures of the chemical structure,
        compares the plurality of substructures to the one or more assigned elemental compositions to find one or more matching substructures,
        assigns the one or more matching substructures to their corresponding assigned elemental compositions,
        scores the one or more matching substructures,
        combines scores of the one or more assigned elemental compositions and their corresponding one or more matching substructures to produce an overall score for each of the one or more assigned elemental compositions,
        selects at least one elemental composition of the one or more assigned elemental compositions that has the highest overall score, and
        converts the mass of the at least one peak to the mass of the selected at least one elemental composition, producing a product ion mass spectrum with higher mass accuracy.

2. The system of claim 1, wherein the one or more assigned elemental compositions are scored based on fragmentation rules comprising one or more of a rule that the elemental composition of a fragment ion is consistent with the composition of a known precursor ion, a rule that losses are consistent with their precursor, a rule that chemical bonds of higher order are harder to break than bonds of lower order, and a rule that chemical bonds between carbon (C) and heteroatoms nitrogen (N), oxygen (O), and sulphur (S) are easier to break than C—C bonds.

3. The system of claim 1, wherein the one or more assigned elemental compositions are scored based on a mass difference between at least one elemental composition and the mass of the at least one peak.

4. The system of claim 2, wherein the processor further receives at least one data collection condition that corresponds to the at least one product ion mass spectrum and the fragmentation rules comprise a rule that uses the at least one data collection condition.

5. The system of claim 4, wherein the at least one data collection condition comprises one or more of a polarity, a first quadrupole Q1 resolution, a precursor mass-to-charge ratio (m/z), an m/z error distribution, a target product ion spectrum Q1 width, and a collision energy.

6. The system of claim 1, wherein after the processor converts the mass of the at least one peak to the mass of the selected at least one elemental composition, the processor further adds one or more isotopic peaks of the at least one peak to the product ion mass spectrum with higher mass accuracy.

7. A method for converting product ion mass spectra to product ion mass spectra with higher mass accuracy, comprising:
    receiving at least one product ion mass spectrum produced by a tandem mass spectrometer using a processor;
    receiving a chemical structure of a compound that corresponds to the at least one product ion mass spectrum using the processor;
    assigning one or more elemental compositions to at least one peak in the at least one product ion spectrum based on the chemical structure using the processor by calculating one or more elemental compositions from the elements of the chemical structure that have masses within a mass tolerance of the mass of the at least one peak and assigning the one or more elemental compositions to the at least one peak;
    scoring the one or more assigned elemental compositions using the processor;
    simulating one or more fragmentations of the chemical structure to produce a plurality of substructures of the chemical structure using the processor;
    comparing the plurality of substructures to the one or more assigned elemental compositions to find one or more matching substructures using the processor;
    assigning the one or more matching substructures to their corresponding assigned elemental compositions using the processor;
    scoring the one or more matching substructures using the processor;
    combining scores of the one or more assigned elemental compositions and their corresponding one or more matching substructures to produce an overall score for each of the one or more assigned elemental compositions using the processor;

selecting at least one elemental composition of the one or more assigned elemental compositions that has the highest overall score using the processor; and converting the mass of the at least one peak to the mass of the selected at least one elemental composition using the processor, producing a product ion mass spectrum with higher mass accuracy.

8. A computer program product, comprising a non-transitory and tangible computer-readable storage medium whose contents include a program with instructions being executed on a processor so as to perform a method for converting product ion mass spectra to product ion mass spectra with higher mass accuracy, comprising:

providing a system, wherein the system comprises one or more distinct software modules, and wherein the distinct software modules comprise an input module and an analysis module;

receiving at least one product ion mass spectrum produced by a tandem mass spectrometer using the input module;

receiving a chemical structure of a compound that corresponds to the at least one product ion mass spectrum using the input module;

assigning one or more elemental compositions to at least one peak in the at least one product ion spectrum based on the chemical structure using the analysis module by calculating one or more elemental compositions from the elements of the chemical structure that have masses within a mass tolerance of the mass of the at least one peak and assigning the one or more elemental compositions to the at least one peak;

scoring the one or more assigned elemental compositions using the analysis module;

simulating one or more fragmentations of the chemical structure to produce a plurality of substructures of the chemical structure using the analysis module;

comparing the plurality of substructures to the one or more assigned elemental compositions to find one or more matching substructures using the analysis module;

assigning the one or more matching substructures to their corresponding assigned elemental compositions using the analysis module;

scoring the one or more matching substructures using the analysis module;

combining scores of the one or more assigned elemental compositions and their corresponding one or more matching substructures to produce an overall score for each of the one or more assigned elemental compositions using the analysis module;

selecting at least one elemental composition of the one or more assigned elemental compositions that has the highest overall score using the analysis module; and converting the mass of the at least one peak to the mass of the selected at least one elemental composition using the analysis module, producing a product ion mass spectrum with higher mass accuracy.

* * * * *